United States Patent [19]

McGuire

[11] Patent Number: 5,562,669
[45] Date of Patent: Oct. 8, 1996

[54] CRUCIATE LIGAMENT RECONSTRUCTION WITH TIBIAL DRILL GUIDE

[76] Inventor: David A. McGuire, 3418 Lakeside Dr., Anchorage, Ak. 99515

[21] Appl. No.: 180,956

[22] Filed: Jan. 13, 1994

[51] Int. Cl.$^6$ .............................. A61B 17/56; A61F 5/00
[52] U.S. Cl. .................. 606/72; 606/86; 606/88
[58] Field of Search ............... 606/72–78, 102, 606/104; 623/13, 16

[56] References Cited

U.S. PATENT DOCUMENTS

| | | | |
|---|---|---|---|
| 4,400,833 | 8/1983 | Kurland | 3/1 |
| 4,605,414 | 8/1986 | Czajka | 623/13 |
| 4,632,100 | 12/1986 | Somers | 606/73 |
| 4,744,793 | 5/1988 | Parr | 623/13 |
| 4,772,286 | 9/1988 | Goble et al. | 623/13 |
| 4,784,126 | 11/1988 | Hourahane | 128/92 |
| 4,927,421 | 5/1990 | Goble et al. | 606/73 |
| 4,946,462 | 8/1990 | Watanabe | 606/148 |
| 4,950,270 | 8/1990 | Bowman | 606/73 |
| 4,950,271 | 8/1990 | Lewis | 606/102 |
| 5,067,962 | 11/1991 | Campbell | 623/13 |
| 5,139,499 | 8/1992 | Small | 606/73 |
| 5,139,520 | 8/1992 | Rosenberg | 623/13 |
| 5,176,682 | 1/1993 | Chow | 606/72 |
| 5,211,647 | 5/1993 | Schmieding | 606/73 |
| 5,282,802 | 2/1994 | Mahony | 606/73 |

FOREIGN PATENT DOCUMENTS

| | | |
|---|---|---|
| 0495487A2 | 7/1992 | European Pat. Off. . |
| 2-246968 | 2/1990 | Japan . |
| 4-59902 | 4/1992 | Japan . |
| 2194445 | 3/1988 | United Kingdom . |

OTHER PUBLICATIONS

Vascularized Patellar Tendon Graft With Rigid Internal Fixation for Anterior Cruciate Ligament Insuffciency, Jul. 29, 1982.

"A New Femoral Drill Guide for Arthroscopically Assisted Anterior Cruciate Ligament Replacement", Howard J. Marans, M.D. et al., *Arthroscopy: The Journal of Arthroscopic and Related Surgery*, 8(2):234–238, 1992.

"Functional Anatomy of the Anterior Cruciate Ligament and A Rationale for Reconstruction", Magnus Odensten, M. D. et al., *Sports and Trauma Research Group*, vol. 67–A, No. 2, Feb., 1985.

*Primary Examiner*—Michael A. Brown
*Attorney, Agent, or Firm*—Bromberg & Sunstein

[57] ABSTRACT

A method of ligament reconstruction in which at least one ligament replacement is extended between two bone plugs and fixed within each of two bone tunnels in the bones of a joint using interference screws. The bone plugs are given two substantially parallel grooves longitudinally in which the ligament replacements are seated. The ligament replacement may be a semitendinosus tendon attached to itself to form a loop attached to each of the two bone plugs. The bone plugs may be autogenous by using a coring reamer when forming the bone tunnels. A bone block drill guide having three parallel columns can be used to form the substantially parallel grooves in the bone plugs. A trefoil rasp has three cutting lobes, two opposite each other and one approximately equidistant from the other two. The rasp forms three channels in the bone tunnels, two for the looped tendon and one for the interference screw. A tibial drill guide directs a coring reamer without use of a guide wire.

22 Claims, 4 Drawing Sheets

5,562,669

CRUCIATE LIGAMENT RECONSTRUCTION WITH TIBIAL DRILL GUIDE

This application is related to U.S. application Ser. No 07/956,733 filed Oct. 2, 1992, which is a continuation-in-part of U.S. applications Ser. No. 806,906, filed Dec. 13, 1991 (now issued as U.S. Pat. No 5,257,996 on Nov. 2, 1993), and Ser. No. 07/839,466 filed Feb. 19, 1992. These applications and patents which all relate to cruciate ligament reconstruction, are hereby incorporated by reference herein.

BACKGROUND OF THE INVENTION

The present invention relates to the field of arthroscopic surgery, particularly anterior cruciate ligament reconstruction.

One common approach to cruciate ligament reconstruction is the use of the patellar tendon to form a bone-tendon-bone graft. This involves cutting out a bone block from the top of the patella. Deviations from proper technique for removal of the patellar bone block have resulted in reports of patellar tendinitis, patellar fractures and even, in some instances, ruptures of the patellar ligament after the grafting procedure. Whether or not these complaints are properly related to the use of the patellar bone block in cruciate ligament reconstruction, these concerns are reason enough to identify an alternate method for performing the surgery.

SUMMARY OF THE INVENTION

The present invention in various embodiments is directed to a bone-tendon-bone composite graft for use in cruciate ligament reconstruction along with a tibial drill guide for forming the tibial tunnel, a trefoil rasp for forming channels in the bone tunnels and a bone block drill guide for forming the bone plugs of the graft. The method of the present invention is directed to ligament reconstruction surgery. In a preferred embodiment, a bone tunnel is formed in each of two bones of the joint. In knee surgery, these are the femur and the tibia. Preferably, the bone tunnel is formed by drilling a core out through the bone such that the core might be used to form the bone plug in the composite graft. The bone plugs are machined to form two longitudinal substantially parallel grooves opposite one another. At least one ligament replacement, such as a semitendinosus tendon, and/or gracilis, is extended between both of two bone plugs along the parallel grooves in each plug. The ligament replacement is attached to the two bone plugs. Each bone plug is inserted into one of the bone tunnels and secured therein by an interference screw. The use of the bone-tendon-bone composite graft of the invention results in a reconstructed cruciate ligament, also, in accordance with an embodiment the present invention.

The invention further includes in another embodiment a bone block drill guide for forming the bone plugs required in the composite graft of the present invention. The bone block drill guide includes a main hole for accommodating the bone plug. First and second parallel holes that intersect opposite sides of the main hole are used for directing a drill bit to cut a groove longitudinally along the bone block.

A trefoil rasp in accordance with an embodiment of the present invention is used to file channels in the bone tunnels. Two channels, oppositely located from one another, accommodate the ligament replacement attached between the two bone grafts. The third channel is generally located parallel to and equidistant from the other two channels. This third channel is used to guide an interference screw along the bone tunnel adjacent to the bone portion of the graft.

The composite graft in accordance with an embodiment of the present invention is advantageously formed without cutting into the patella. The trefoil rasp provides for interference screw fixation without permitting the screw to cut into the ligament replacement.

Other features of the present invention will become apparent during the following description taken in conjunction with the drawings.

BRIEF DESCRIPTION OF THE DRAWINGS

FIG. 3b is an end view of the rasp of FIG. 3a.

FIG. 4b is a side view of the bone plug of FIG. 4a.

FIG. 7b is a plan view of the bone block drill guide of FIG. 7a.

DETAILED DESCRIPTION OF THE PREFERRED EMBODIMENTS

Figure 1:
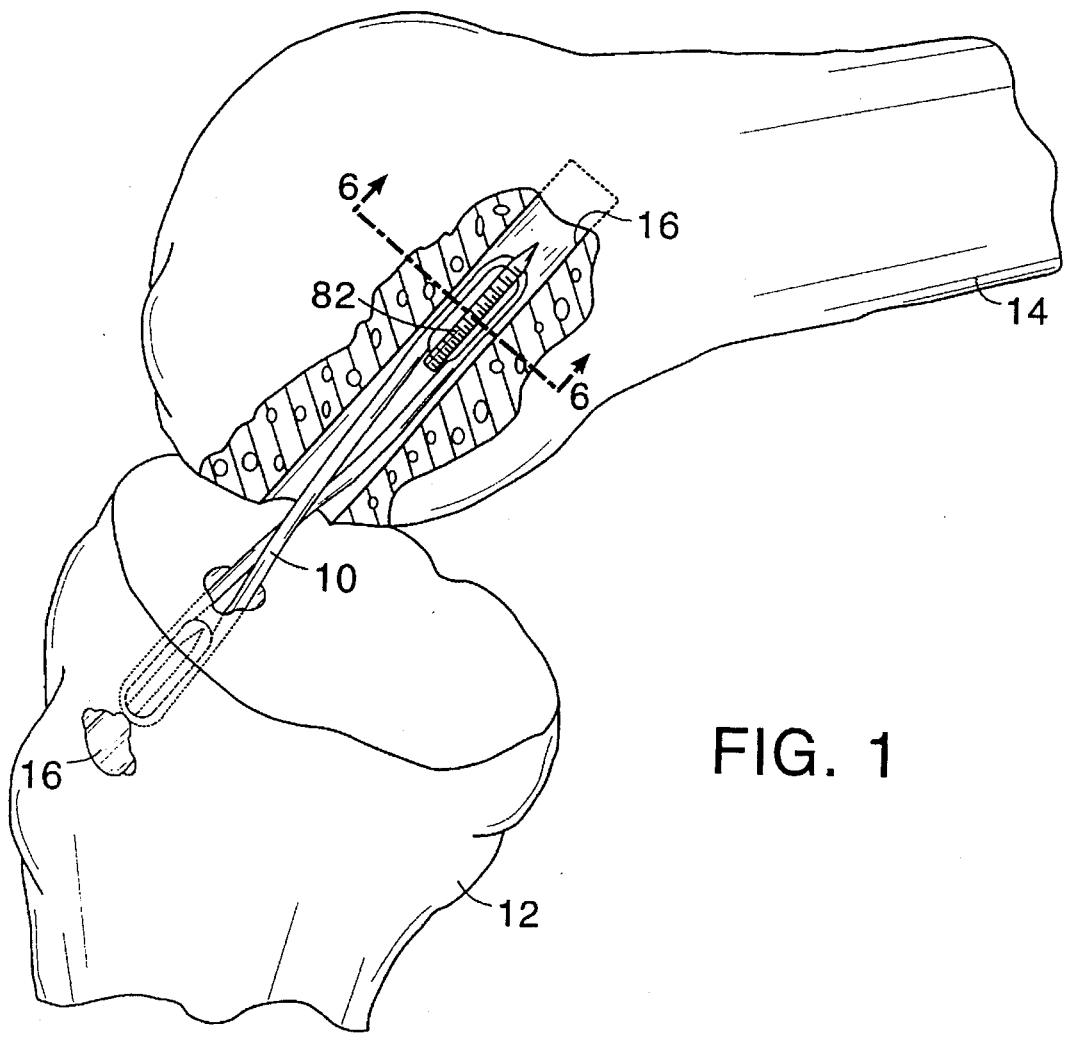
FIG. 1 is a perspective view in partial cross section of a reconstructed ligament of the present invention.

Referring now to the drawings, a reconstructed ligament 10 for a knee joint is shown in FIG. 1 in accordance with an embodiment of the present invention. The cruciate ligament reconstruction surgical operation can be conducted as an open surgery, or preferably, through arthroscopic surgery. The arthroscopic surgical method presently preferred for carrying out the present invention shall now be described.

Arthroscopic diagnostic procedures are first conducted without tourniquet control in order to allow sufficient time for the ACL reconstruction procedure. Conventional anteromedial and distal lateral portals are drilled to give access to the knee joint for these procedures. The procedures may include meniscotomy, meniscal repair, removal of loose bodies, debridement of anterior cruciate ligament tear, etc. Notchplasty may be commenced under tourniquet control. The boundary of the notchplasty should be sufficiently wide (about 2 cm.) and sufficiently posterior to include the posterior lateral femoral cortex in order to ensure accurate placement and subsequent isometry.

In order to proceed with anterior cruciate ligament reconstruction, a vertical incision is made medial to the tibial tubercle approximately 2.5 cm. in length. The skin incision may be undermined in such a fashion as to provide sufficient mobility for retraction, while harvesting the tibial and femoral bone cores. A carefully placed anteromedial tibial incision may begin approximately 1 cm. medial to the tibial tubercle and 2 cm. distal to the joint line. Conventional surgical procedures are used to excise a semitendinosus tendon, and, if desired, the accompanying gracilis. While the use of the semitendinosus tendon and gracilis is one embodiment of the invention, alternative ligament replacement materials may be substituted for use in the composite graft of the invention.

The two major bones that meet at the knee joint are the tibia 12 and the femur 14. A bone tunnel 16 is drilled through each of these two bones. The tunnels 16 may be drilled with a regular drill that crushes and removes the bone within the tunnel. However, it is preferable to use a coring reamer to drill the bone tunnels. The reamer drills out a core of bone through each of the bone tunnels. The bone core can then be used to form a bone plug in the composite graft that will be replaced when reconstructing the ligament. In using the coring reamer to drill out a core that may be reused in the composite graft, it is important that a guide pin not be inserted into the core for directing the reamer. The hole formed by the guide pin through the center of the core would form a stress riser in the bone plug making the bone plug subject to fracture. A tibial guide 30 in accordance with an embodiment of the present invention properly orients and guides a coring reamer for making the bone tunnels without a guide wire.

Figure 2:
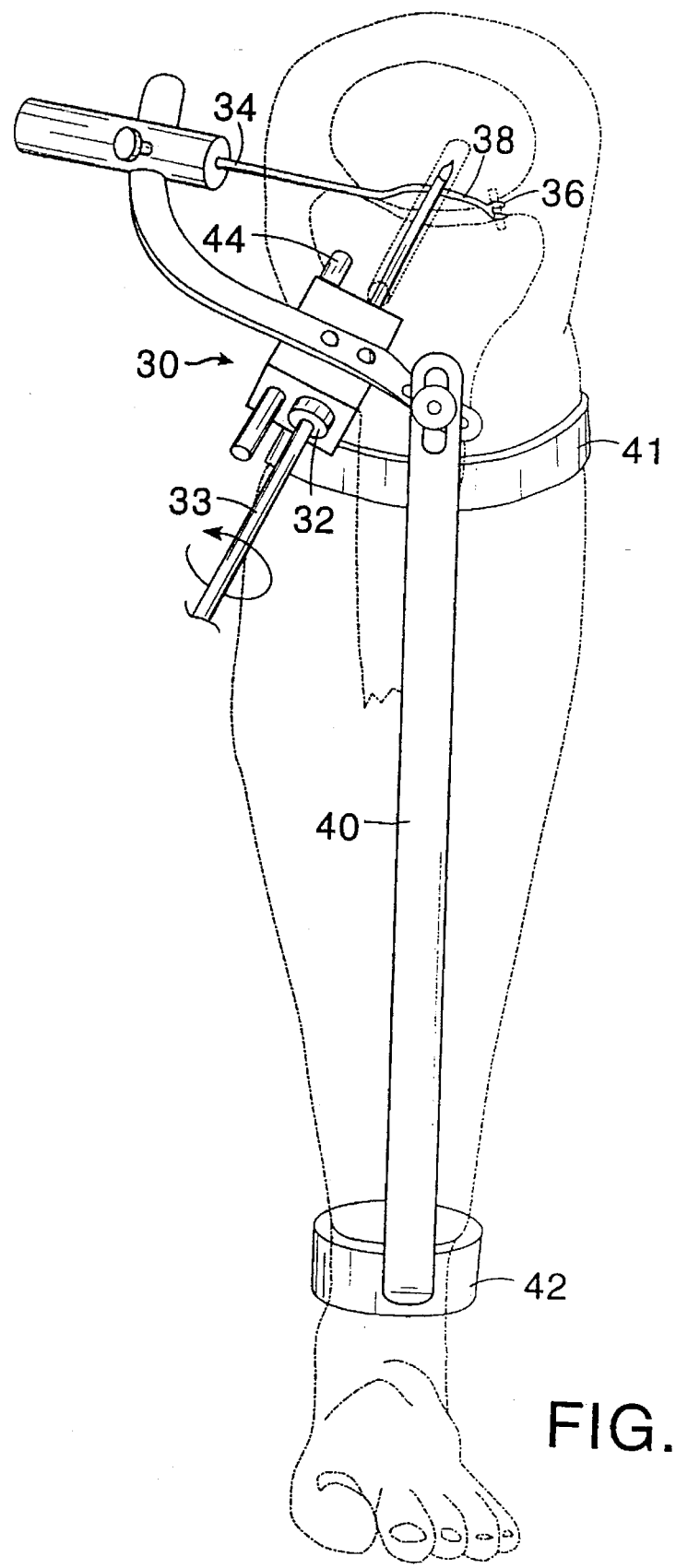
FIG. 2 is an isometric view of a tibial drill guide of the present invention.

Referring now to FIG. 2, the tibial guide 30 is shown. A pipe 32 is oriented at approximately 55° to horizontal. The pipe 32 serves to guide a coring reamer 33 or other drill inserted therethrough. With the patient's leg held fixed at approximately 110° to 120°, the guide can be used for drilling both the tibial tunnel and then the femoral tunnel. Therefore, a portal for the drill is not required behind the femur and a closed tunnel can be drilled. Both tunnels are drilled through the tibia from the anteromedial tibial incision.

A positioning arm 34 is attached to the pipe 32. The positioning arm 34 has a fork 36 at its far end. The fork 36 has two rounded prongs. The fork 36 is attached to an arcuate portion 38 of the arm 34. The arcuate portion 38 allows for maneuverability of the arm 34 within the knee area upon insertion through the anteromedial portal. Meanwhile, the arthroscope is inserted into the knee joint through the distal lateral portal. The fork 36 needs to be placed against the leading edge of the posterior cruciate ligament. The positioning arm 34 is shaped and oriented with respect to the pipe 32 so that the hole drilled by a reamer or drill through the pipe 32 is directed through the tibia to a point approximately 7 millimeters from the leading edge of the posterior cruciate ligament. The center of the tibial tunnel is further defined by the tangent to the center of the inner circumference of the anterior one-third of the lateral meniscus.

An adjustable rod 40 is attached to the pipe 32 at one end. A calf strap 41 secures the guide to the patient's leg. The guide has an ankle strap 42 proximate the opposite end of the rod 40. The rod 40 can be adjusted in length to accommodate different leg sizes. The calf strap 41 and ankle strap 42 provide anchors for achieving and maintaining proper orientation of the pipe 32. The straps are affixed with the fork 36 oriented properly around the PCL attachment on the tibia.

Another anchor to securely orient the pipe 32 is provided by a K-wire 44. The K-wire 44 is shot through the skin of the patient's leg and into the tibia. The K-wire 44 may be positioned on the guide 30 closely adjacent the pipe 32 so that the hole formed in the tibia by the K-wire is adjacent and parallel to the hole to be drilled through the pipe 32. The anchoring provided by the cup 36, the ankle strap 42 and the K-wire 44 stably and correctly position the pipe 32 for guiding a coring reamer or a drill. The tunnels may thus be cored without a guide pin in the core. The tibial tunnel is reamed first and the core removed. The knee is flexed or extended a variable amount in order to properly position the femoral tunnel. A longer coring reamer is then directed through the tibial tunnel for drilling in and through the femur. The bone core from the femur is removed. Standard deburring and debridement procedures are followed.

Figure 4A:
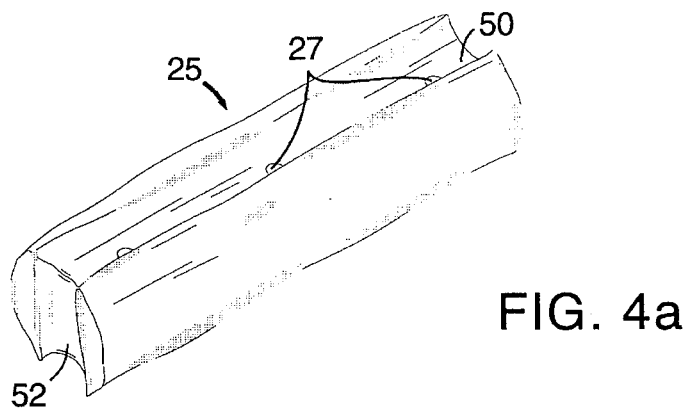
FIG. 4a is an isometric view of a bone plug for use in the invention.
Figure 4B:
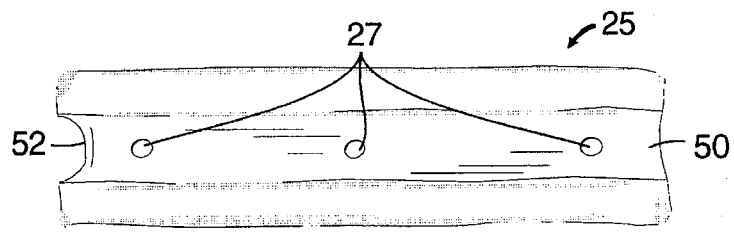

If cores have been drilled out from the bone tunnels they may be used for the bone plugs 25 otherwise, donor bone, namely allograft bone, can be used to make the bone plugs. Referring now to FIGS. 4a and 4b, whatever bone plug 25 is used, two longitudinal substantially parallel grooves 50 are drilled on opposite sides of each bone plug. The grooves provide a recess in which the semitendinosus tendon 20 and gracilis 21 can be seated. A notch 52 may also be drilled, if desired, across one end of the bone plug so that the tendon can be wrapped alongside and around the end of the bone plug, without protruding excessively from the plug. The notch 52 is not required because the bone tunnel is open at each end providing no restriction on the tendon projecting above the end of the graft. It is also advantageous to provide suture holes 27 through the bone plug for attaching the tendon to the plug. The suture holes 27 are drilled into the grooves radially through the bone plug and from one of the substantially parallel grooves 50 to the other. In a presently preferred embodiment, three such suture holes are drilled through the bone plug.

Figure 7A:
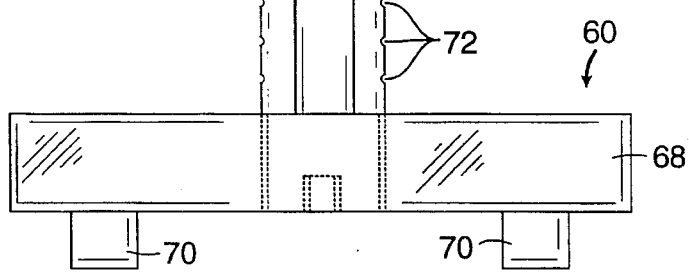
FIG. 7a is a side view of the bone block drill guide of the present invention.
Figure 7B:
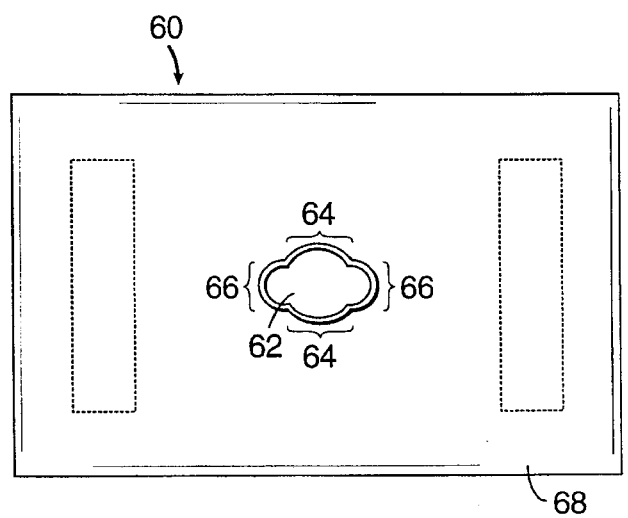

In order to easily and efficiently form a bone core into the desired bone plug for a composite graft, a bone block drill guide 60 of the invention as shown in FIGS. 7a and 7b may be used. The drill guide 60 features a central substantially cylindrical column 62. The central column 62 includes a pair of opposing curved walls 64 having a center of curvature substantially coincident with the center axis through the column 62. The curved walls 64 are shaped so as to hold a bone core parallel with the axis of the column and substantially centered within the column. A second pair of opposing curved walls are arranged at 180° to each other with respect to the central column formed by the curved walls 64. This second pair of walls are the drill guide walls 66. The drill guide walls 66 form two parallel columns on opposite sides of the central column. The drill guide walls 66 have a shorter radius of curvature than the first pair of opposing curved walls 64. In accordance with a presently preferred embodiment, the inner diameter of the drill guide walls 66 is 6 mm whereas the inner diameter of the first pair of opposing walls 64 is 11 mm. The central column 62 is mounted over a base 68. A bone core standing in the central column 62 rests on the base 68. The base 68 is provided with holes therethrough in alignment with the open circular cylinder formed within the drill guide walls 66. The base 68 may also include legs 70 for supporting the drill guide over a table. For drilling suture holes through the bone block, holes 72 are arranged horizontally through the drill guide walls 66. Three holes 72 are preferably aligned in a line.

The substantially parallel grooves 50 are drilled by inserting the bone core or allograft into the center chamber of the column 62 formed by the opposing curved walls 64. A drill is directed in the column 62 along each of the drill guide walls 66 in succession. Thus, parallel grooves 50 are formed on opposite sides of the bone core. The drill may be equipped with a stop to prevent the drill from being directed too far down through the column where it may contact the table beneath. A drill bit inserted through the holes 72 can be easily directed through the center of a groove drilled along the bone core. The suture holes drilled through guide holes 72 preferably extend from one groove to the opposite groove in the bone block.

Figure 5:
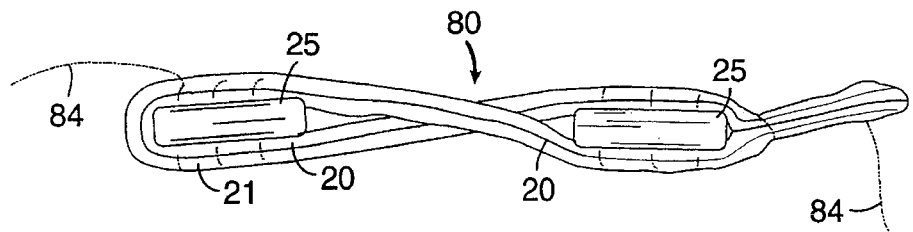
FIG. 5 is a side view of a bone-tendon-bone composite graft of the present invention.

The semitendinosus tendon 20 and/or gracilis 21 is extended between both of the bone plugs 25. The tendons are seated inside the two substantially parallel grooves 50 and about an end of each bone plug. The tendons are preferably sutured to themselves to form a double loop as shown in FIG. 5. Sutures are also used through the suture holes to attach the tendon to each of the bone plugs. The tendon strands may be straight or twisted between the bone plugs. Twisting will shorten the length of the graft. A ligament replacement of an embodiment of the invention may include both the semitendinosus tendon and the gracilis. As such four strands will connect the two bone plugs. Other embodiments of the invention may use one or the other of the semitendinosus tendon and gracilis. Still further embodiments of the invention may substitute or combine man made or artificial fibers or human tissue for the tendons for use as the ligament replacement.

Figure 3A:
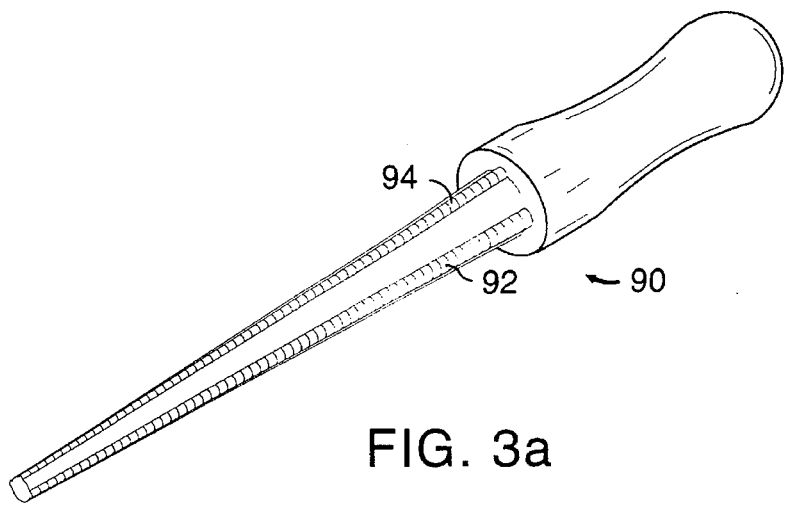
FIG. 3a is an isometric view of a trefoil rasp of the present invention.
Figure 3B:
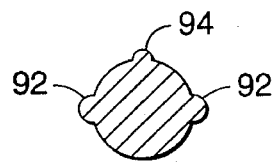

In affixing the composite graft 80 within a bone tunnel, contact between a screw 82 and the tendon should be avoided so as not to cut or tear the tendon. To better insure that the screw is out of contact with the tendon, an interference screw should be driven along the bone portion of the graft between the graft and the bone tunnel wall. A trefoil rasp 90 of the present invention is recommended for use prior to fixation of the graft. As shown in FIGS. 3a and 3b, the trefoil rasp 90 has three longitudinal lobes for use in cutting three channels into each of the bone tunnels. Reciprocating movement of the trefoil rasp 90 in and out of the bone tunnels 16 serves to file away the tunnel walls to form the desired channels. Two of the longitudinal lobes 92 are 180° apart on the rasp. These longitudinal lobes 92 are used to form channels for accommodating the semitendinosus tendons 20 and gracilis 21 seated in the parallel grooves of the bone graft. When the gracilis 21 is attached along and on top of the semitendinosus tendon 20, the channels are required to provide room for the graft to fit within the tunnel.

Figure 6:
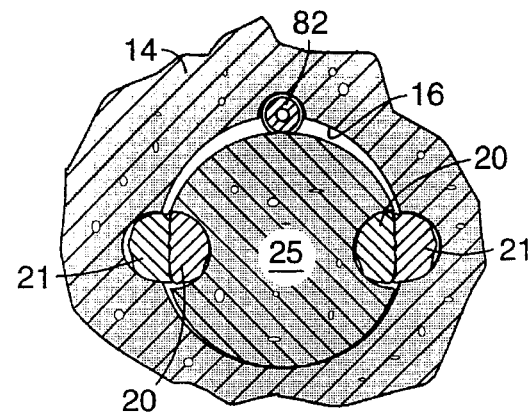
FIG. 6 is a cross-sectional view of FIG. 1 taken along lines 6—6.

The third longitudinal lobe 94 is located parallel to and equidistant from the two opposed lobes. Looking at the end of the rasp as in FIG. 3b, the third lobe 94 is preferably 90° to each of the other two lobes. In the presently preferred embodiment, the third lobe 94 projects 2 mm. from the rasp shaft whereas the other two lobes 92 each project 3 mm. from the shaft. The third lobe 94 advantageously files away a channel along which an interference screw is driven as shown in FIG. 6. The channel helps to maintain the screw straight adjacent the bone portion of the graft. Advantageously, the tibial guide 30 and the trefoil rasp 90 can complement one another in forming the channel for the screw. The hole formed by the K-wire 44 of the tibial guide may be used as the screw channel. To achieve this result, the trefoil rasp should be aligned in the tibial tunnel with its third lobe 94 overlapping into the K-wire hole.

After the channels have been filed in the bone tunnels, the sutures 84 hanging from one end of the composite graft are attached to a needle, a passer or other conventional graft placement tool. The passer is inserted through tibial and femoral bone tunnels and out through the skin on the posterior side of the knee. The passer is removed leaving the suture hanging from the posterior end of the graft and a suture at the other end of the graft hanging out through the tibial incision. The sutures may be pulled on to properly tension and locate the graft within the bone tunnels. Alternatively, the graft may be positioned within the bone tunnels using a pushing device instead of a suture pulling the graft into position.

Fixation of the graft is preferably accomplished with a headless cannulated interference screw. The cannulated interference screw can be carried by a guide wire extending from the tip of an angled driver. The guide wire is preferably a springy wire made of a material such as Nitinol™. The wire extends about 2 centimeters past the end of a screw carried by the driver. For securing the interference screw in the femoral tunnel, the angled or flexible driver and screw are preferably inserted through the anteromedial portal. An angled driver and use thereof is described in co-pending U.S. patent application Ser. No. 07/956,733 filed Oct. 2, 1992, the entire disclosure of which has been incorporated by reference herein. A flexible slide may be used to provide a track to follow from the anteromedial portal to the channel in the femoral tunnel for the interference screw. The insertion of a flexible slide simplifies the guidance of the interference screw into the channel of the femoral tunnel. Once the screw is properly positioned in the tunnel, the driver can initiate screwing and the slide can be removed. The oppositely located channels in the femoral tunnel hold the semitendinosus tendon in position away from the interference screw as it is screwed between the bone portion of the graft and the channel of the bone tunnel. Upon fixation of the interference screw in the femoral tunnel, the angled driver is removed.

The proper tension is then applied to the graft by pulling on the suture hanging out from the tibial incision. A driver and a headless cannulated interference screw are then inserted through the tibial incision for driving the screw along the channel formed in the tibial tunnel. The sutures are cut and the incisions are closed. The reconstructed knee upon fixation of the graft appears as in FIG. 1.

While this operation has been discussed in terms of using autogenous bone cores, alternative sources of bone plugs may be substituted. Allografts, in which donor bone is freeze-dried or fresh frozen for preservation, are one alternative. The freeze drying process kills cells in the bone and may reduce the risk of transmission of infection. Another alternative bone plug is the use of synthetic graft material. With any of these alternatives, the bone plugs may be shaped to appear as described above for the autogenous graft. With the allograft and the synthetic graft, the coring reamer is no longer required and an ordinary drill may be used instead for drilling the bone tunnels.

The surgical technique of the present invention advantageously makes use of the fact that the semitendinosus and gracilis has less morbidity associated with harvesting than does the patellar tendon. It is further advantageous to use a coring reamer and a bone block drill guide of the invention to remove the bone cores from the bone tunnels in the tibia and femur and shape them to accommodate the semitendinosus tendon. The trefoil rasp provides the still further advantage of maintaining alignment of the graft and interference screws in the bone tunnel so that the screw is directed adjacent only the bone portion of the graft.

Of course, it should be understood that various changes and modifications to the preferred embodiments described above will be apparent to those skilled in the art. For example, the bone blocks in the composite graft may be autogenous, allogenic or synthetic. The tendon or other ligament replacement used on the graft may be one or more strands sutured to both of the bone blocks along the grooves. Moreover, alternative equipment may be used for drilling the grooves and the bone plugs. These and other changes can be made without departing from the spirit and the scope of the invention and without diminishing its attendant advantages. It is therefore intended that such changes and modifications be covered by the following claims.

I claim:

1. A method for ligament reconstruction in a joint of a body comprising the steps of:
   forming a bone tunnel in each of two bones of the joint;
   providing first and second bone plugs, each having two longitudinal substantially parallel grooves opposite one another on said each bone plug;
   extending at least one ligament replacement between both of the first and second bone plugs along the two substantially parallel grooves in each bone plug;
   attaching the at least one ligament replacement to the first and second bone plugs;
   inserting the first bone plug into one of the bone tunnels;
   screwing an interference bone fixation screw in between a wall of said one of the bone tunnels and an exposed bone portion of the first bone plug;
   inserting the second bone plug into a second one of the bone tunnels;
   screwing an interference bone fixation screw in between a wall of said second one of the bone tunnels and an exposed bone portion of the second bone plug.

2. The method of claim 1 wherein said step of forming a bone tunnel comprises drilling out a core through each of the two bones.

3. The method of claim 2 wherein said step of providing comprises inserting each of the bone cores into a central column of a bone block drill guide and for each bone core, drilling through each of two parallel cylindrical columns positioned opposite one another adjacent the central column of the bone block drill guide to form two substantially parallel grooves opposite one another along each of the bone cores, thereby forming said first and second bone plugs.

4. The method of claim 1 further comprising removing a semitendinosus tendon from the body for use as the at least one ligament replacement and wherein said step of extending comprises extending the semitendinosus tendon around both of the first and second bone plugs along the two substantially parallel grooves in each bone plug.

5. The method of claim 4 further comprising suturing the semitendinosus tendon to itself to form a loop.

6. The method of claim 4 wherein the at least one ligament replacement further includes a gracilis and wherein said step of extending further comprises extending the gracilis along the semitendinosus tendon around both of the first and second bone plugs.

7. The method of claim 1 further comprising forming three longitudinal channels along each of said bone tunnels, two of said three longitudinal channels being opposite one another and a third of said three longitudinal channels being about equidistant from the two of said three longitudinal channels.

8. A method for ligament reconstruction in a joint of a body comprising the steps of:
   coring out a bone tunnel in each of two bones of the joint to remove first and second bone cores;
   attaching at least one ligament replacement between both of the first and second bone cores;
   inserting the first bone core into one of the bone tunnels;
   fixing the first bone core within said one of the bone tunnels;
   inserting the second bone core into a second one of the bone tunnels; and
   fixing the second bone core within said second one of the bone tunnels.

9. The method of claim 8 further comprising the step of forming two longitudinal substantially parallel grooves opposite one another in each of said first and second bone cores and wherein the at least one ligament replacement is seated within the parallel grooves when attached to the first and second bone cores.

10. The method of claim 9 wherein said step of forming comprises inserting each of the bone cores into a central column of a bone block drill guide and for each bone core, drilling through each of two parallel cylindrical columns positioned opposite one another adjacent the central column of the bone block drill guide to form the two longitudinal substantially parallel grooves along each of the bone cores.

11. The method of claim 8 wherein said step of fixing the first bone core comprises screwing an interference screw in between a wall of said one of the bone tunnels and the first bone core.

12. The method of claim 8 further comprising removing a semitendinosus tendon from the body for use as the at least one ligament replacement and wherein the step of attaching comprises extending the semitendinosus tendon around both of the first and second bone cores to form a loop and suturing the loop of tendon to each of the two bone cores.

13. The method of claim 8 further comprising forming three longitudinal channels along each of said bone tunnels, two of said three longitudinal channels being opposite one another and a third of said three longitudinal channels being about equidistant from the two of said three longitudinal channels, 14. A composite graft comprising:
   first and second bone plugs, each having two substantially parallel longitudinal grooves formed along opposite sides of said each bone plug and lacking any other longitudinal holes cut therein; and
   a ligament replacement formed in a loop, said ligament replacement extending around said first and second bone plugs along said grooves and being sutured to each of said first and second bone plugs.

15. The composite of claim 14 wherein said first and second bone plugs further comprise at least one suture hole drilled radially through each of said bone plugs from one of the longitudinal grooves through to the other substantially parallel longitudinal groove.

16. The composite graft of claim 14 wherein said first and second bone plugs further comprise a notch in one end to accommodate said ligament replacement extending around said bone plug from one longitudinal groove to the other substantially parallel longitudinal groove.

17. The composite graft of claim 14 wherein said ligament replacement comprises a semitendinosus tendon.

18. The composite graft of claim 17 wherein said ligament replacement further comprises a gracilis.

19. A reconstructed cruciate ligament comprising:
   first and second bone plugs;
   a tibia having a tunnel therethrough in which said first bone plug is inserted;
   a screw forming an interference fixation between the first bone plug and the tunnel in said tibia;
   a femur having a tunnel therethrough in which said second bone plug is inserted;
   a screw forming an interference fixation between the second bone plug and the tunnel in said femur;
   a first ligament replacement strand extending between said first and second bone plugs and attached longitudinally alongside each of said first and second bone plugs; and
   a second ligament replacement strand extending between said first and second bone plugs and attached longitudinally along each of said first and second bone plugs opposite from said first ligament replacement strand.

20. The reconstructed ligament of claim 19 wherein said first and second bone plugs each have two substantially parallel longitudinal grooves alongside which said first and second ligament replacement strands are oppositely located.

21. The reconstructed ligament of claim 20 wherein said first and second bone plugs each have at least one suture hole extending radially through said bone plug from one of the longitudinal grooves through to the other substantially parallel groove and wherein a suture extends through the suture hole in each of said bone plugs and said first and second ligament replacement strands to attach said first and second ligament replacement strands to said first and second bone plugs.

22. The reconstructed ligament of claim 20 wherein said first and second ligament replacement strands are formed by a semitendinosus tendon looped around said first and second bone plugs.

* * * * *